United States Patent [19]

Duinker et al.

[11] 4,164,657

[45] Aug. 14, 1979

[54] APPARATUS FOR TOMOGRAPHY

[75] Inventors: Simon Duinker, Bloemendaal; Hendrik Mulder, Delft, both of Netherlands

[73] Assignee: N.V. Optische Industrie "De Oude Delft", Netherlands

[21] Appl. No.: 795,217

[22] Filed: May 9, 1977

[30] Foreign Application Priority Data

May 17, 1976 [NL] Netherlands .................. 7605253

[51] Int. Cl.² .............................................. A61B 6/02
[52] U.S. Cl. ...................... 250/445 T; 250/416 TV; 358/111
[58] Field of Search ............ 250/445 T, 416 TV, 397, 250/369; 358/111

[56] References Cited

U.S. PATENT DOCUMENTS

| | | | |
|---|---|---|---|
| 2,281,931 | 5/1942 | Frank | 250/445 T |
| 2,555,545 | 6/1951 | Hunter et al. | 250/397 |
| 3,058,021 | 10/1962 | Dunn | 358/111 |
| 3,076,054 | 1/1963 | Simon | 358/111 |
| 3,622,786 | 11/1971 | Walker et al. | 358/111 |
| 3,720,831 | 3/1973 | Miraldi | 250/369 |
| 3,778,614 | 12/1973 | Hounsfield | 250/445 T |
| 4,000,425 | 12/1976 | Craig | 250/445 T |

OTHER PUBLICATIONS

"Picture Processing for Radiology," *Hughes Focus*, vol. 1, No. 3, June 20, 1973. Hughes Aircraft Co., Oceanside, Calif.

*Primary Examiner*—Alfred E. Smith
*Assistant Examiner*—T. N. Grigsby
*Attorney, Agent, or Firm*—O'Brien & Marks

[57] ABSTRACT

An apparatus for tomography, comprising an X-ray or gamma-ray source, at least one detector, and an image reconstruction apparatus. The detector is a spatially two-dimensional, continuous detector large enough to form a complete picture of the projection of the object section thereon, taking into consideration the place of the object section and of the source of radiation relative to the detector. The detector is connected by optical or fibre-optical means to a luminance intensifier tube. This tube may be coupled, either optically or fibre-optically, to a television pick-up tube whose output is coupled to the image reconstruction apparatus. In one form of the invention the detector is an X-ray screen, which is preferably concave towards the source of radiation.

19 Claims, 4 Drawing Figures

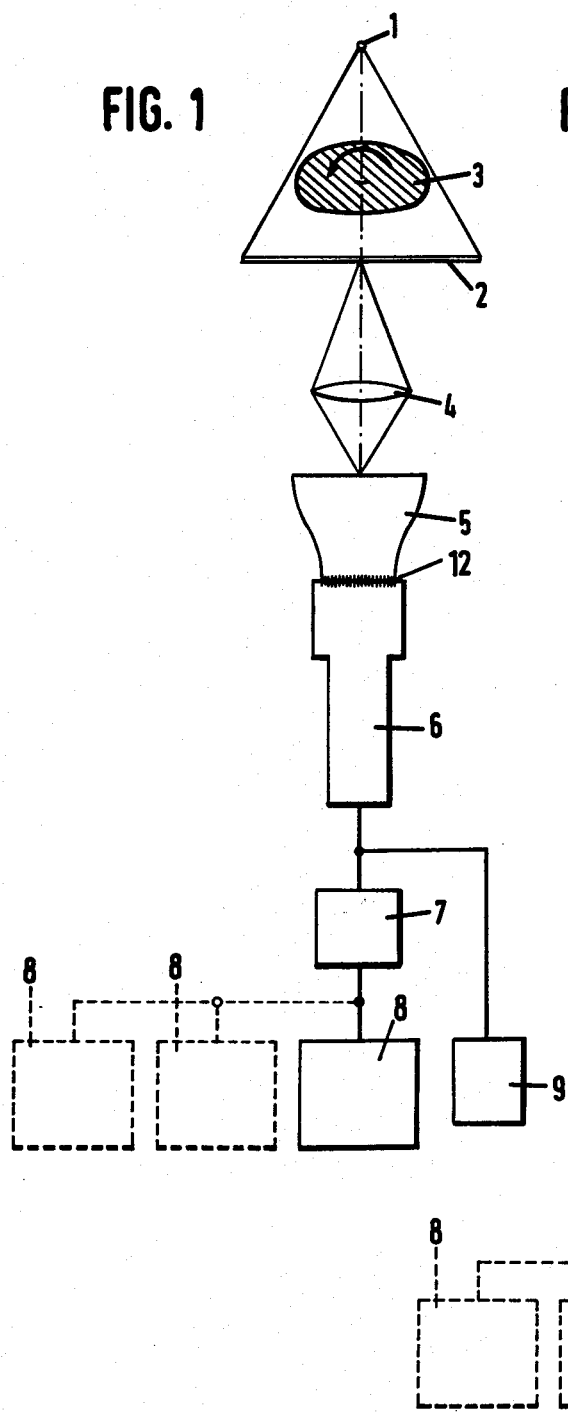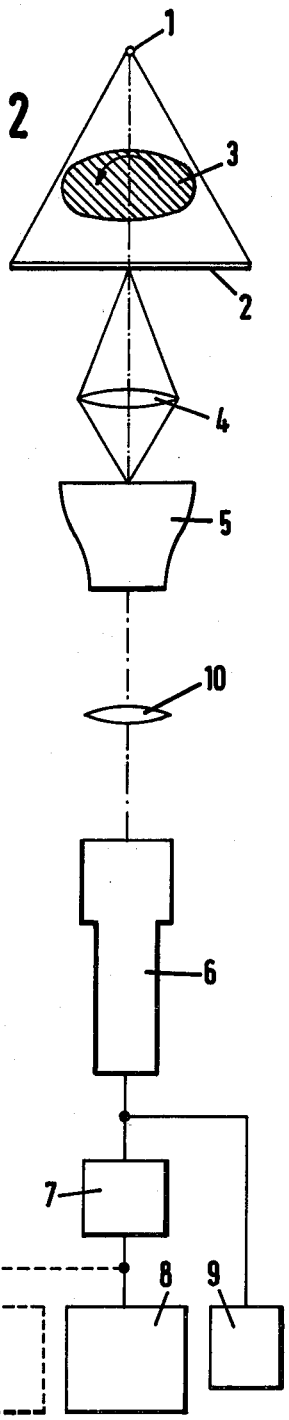

APPARATUS FOR TOMOGRAPHY

This invention relates to an apparatus for tomography, comprising an X-ray or gamma-ray source, at least one detector, and an image reconstruction apparatus.

Such an apparatus is used in the X-ray technique of medical diagnosis for obtaining an image of a disk-shaped section of a patient in which the opacity of the tissues, organs and bones therein to X-rays or gamma-rays is shown as a function of the position thereof within the section.

In this technique it is conventional for the X-ray transmission in the plane of this section to be measured in a large number of directions, which is effected by rotating either the X-ray source and the detector or detectors relatively to the patient, or the patient relatively to the parts referred to. The data thus produced are normally processed by a computer for the reconstruction of the desired image of the section.

It is clear that it is of essential importance that each element of the section can contribute to the X-ray absorption. For if this is not the case, the information is incomplete and no accurate image reconstruction is possible. To realize this object, use can be made of a large number of detectors, or some detectors may be arranged to perform a translatory movement in addition to a possible rotary movement. It will be clear that such a combined movement is time-consuming, and in addition complicates the construction of the apparatus.

It has been found that the number of necessary transmission measurements is substantially proportional to the total number of desired image elements of the reconstructed image, while the computer time required for image reconstruction increases at least proportionally to the number of image elements.

The above construction with a stationary array of discrete detectors has the drawback that the compromise between resolving power and computer time is optimal for one magnification of the section only. For when the distance between the object and the array of detectors is varied, the computer time does not, but the resolving power does vary as a result of the varying geometrical magnification in a diverging beam of X-rays.

As an apparatus of the above type can only produce an image of a thin "slice" of the patient, it will generally be necessary to make a plurality of such sections to produce a total image of a larger area of the patient. For this purpose the patient may be displaced axially relatively to the X-ray source and the detectors by a distance corresponding to the thickness of the section. This thickness determines the number of sections required, and is a compromise between the total period of occupancy of the apparatus and the resolving power.

A disadvantage of such an incremental displacement of the patient relative to the X-ray source and the detectors is that the resolution in the axial direction is constant throughout the section, and local refinement is not, therefore, possible. Thus a piece of tissue exhibiting a large difference in X-ray absorption relative to its surroundings, and terminating, for example, halfway in a reconstructed section, will adversely affect the radial resolution in that section.

Another disadvantage of the above-described stepwise method is that frequently it only turns out later what should have been the optimum magnitude of the steps. If, for example, the object under scrutiny does not change, or only slightly so, in the axial direction concerned, a greater step and a longer measuring time per section, and hence a better signal-to-noise ratio, can be conducive to more accurate image reconstruction.

It is an object of the present invention to provide an apparatus that does not suffer from the above drawbacks and disadvantages, and moreover has a number of additional advantages, such as, for example, relatively inexpensive construction, rapid and reliable operation, low dosage of radiation, which advantages will be described in more detail hereinafter.

According to the invention, there is provided an apparatus for tomography, comprising an X-ray or gamma-ray source, at least one detector, and an image reconstruction apparatus, wherein said detector is a spatially two-dimensional, continuous detector, having dimensions selected in relation to the disposition of the object section to be examined and of the source of radiation relative to the detector so that the projection of the object section, as far as its greatest cross-sectional dimension is concerned, is at least completely depicted on the detector.

By "continuous" is to be understood in this context that the dimensions of, and the relative distances between, the detector elements are small relative to the resolving power of the apparatus.

In one embodiment of the present invention, the detector is arranged outside the envelope of a luminance intensifier tube, and the apparatus is provided with an optical system for depicting the side of the detector away from the source of radiation on the cathode of the luminance intensifier tube.

In another embodiment of the invention, the detector is arranged on the exterior surface of the input window of luminance intensifier tube, said input window being a fibre-optics arrangement for transmitting the radiation image from the detector to the cathode surface of the luminance intensifier tube.

In still another embodiment of the invention, the detector is an X-ray screen.

In yet another important embodiment of the invention, the anode end of the luminance intensifier tube is optically coupled to a television pick-up tube, the output of the latter being coupled to the image reconstruction apparatus.

In still another embodiment of the invention, the luminance intensifier tube is fibre-optically coupled to the television pick-up tube. It is also possible, according to the invention, however, for the luminance intensifier tube to be coupled to the television pick-up tube by means of a lens system.

In another preferred embodiment of the invention, the screen is concave towards the source of radiation, and the screen is preferably exchangeable.

Furthermore, it is a preferred feature of this invention that a television monitor, too, is coupled to the output of the pick-up tube.

Also, according to the invention, a plurality of image reconstruction apparatuses may be connected to the output of the television pick-up tube or to the output of a logarithmic intensifier connected to the output of the televison pick-up tube, whereby to produce images of different sections of the object simultaneously.

An apparatus according to the invention, as described hereinbefore, has a number of advantages over and above apparatuses proposed earlier for the object stated.

Thus, owing to the fact that, in the apparatus of this invention, the combined translatory and rotary movements of prior apparatuses are avoided, a shorter time is needed to obtain all information required for the reconstruction of a complete tomographic section, as a consequence of which blurring is reduced. This advantage of reduced image movement caused, for example, by the patient's breathing, is enhanced still further, if, during operation, it is not the apparatus that is rotated around the patient, but the patient is rotated around his longitudinal axis relatively to the stationary apparatus, inasmuch as, owing to the much smaller moment of inertia, a relatively short period of revolution can thus be realized in a relatively inexpensive manner.

Another advantage of the apparatus according to this invention as compared with conventional CAT scanners is that continuous relative movement between the patient and the source and detector is possible. This means that the data need not be collected on the basis of discrete steps of the source-detector arrangement, as required with digital processing with discrete detector systems.

Still another advantage of the apparatus of this invention is that it enables scanning a plurality of sections at the same time. This is a very essential point of difference from conventional CAT scanners, which is rendered possible by the two-dimensional extent of the detector surface.

When the apparatus according to the invention is provided with a television pick-up tube, then, as a result of the time integration that occurs therein, a lower dosage of radiation can be used during scanning than when a plurality of discrete detectors is used.

Furthermore, when a television pick-up tube is used, the thickness of the section can be selected with reference to the number of television lines that is taken together. If, at a particular position of a section, fewer television lines are taken together than in the rest of the section, resolution can be improved in that particular area of the section.

On the other hand, it is also possible to take more television lines together in a particular portion of a section, whereby to improve the signal-to-noise ratio in areas of slight axial changes. The above can be controlled in a simple manner, for example, by defocussing the scanning beam in the vertical direction to a line of the desired length.

By ensuring that horizontal scanning is always accurately limited to the actual size of the section, optimum adaptation of the resolution is achieved.

Further advantages will be apparent from the following description of some exemplary embodiments of apparatus according to the invention, read with reference to the accompanying drawings. In said drawings, FIG. 1 diagrammatically shows a first embodiment of an apparatus according to the invention;

FIG. 2 shows a second embodiment of an apparatus according to the invention;

Figure 3:
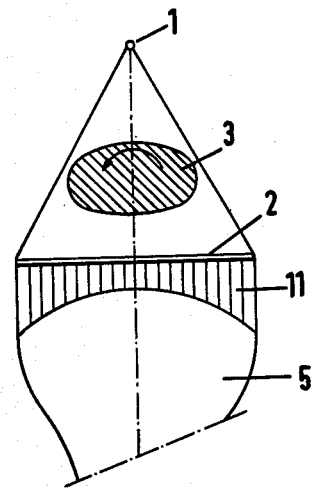
FIG. 3 shows a variant of a part of the apparatus shown in FIG. 1 and 2.

Referring to the drawings, FIG. 1 shows an apparatus according to the present invention, which comprises an X-ray source 1 and an X-ray screen 2, on which screen, during operation of the apparatus, a transmission image of a section of a patient 3, placed between source 1 and screen 2, is obtained.

On the side of the screen away from source 1, there is further provided an optical system 4 of high light-gathering power for depicting the image appearing on the X-ray screen 2 on the photocathode of an image intensifier 5.

In the embodiment of FIG. 1, this image intensifier 5 is coupled direct by fibre-optics means, as shown at 12, to a subsequent television pick-up tube 6. This television tube serves for scanning the image appearing on the anode screen of image intensifier 5 during operation of the apparatus, in the manner conventional in television technique. Tube 6 thus provides a video signal, which is supplied to a monitor 9 and to a logarithmic video amplifier 7, which in turn, as shown in the figure, is coupled to one or more image reconstruction apparatuses 8. From the video signals received, each image reconstruction apparatus then forms a tomogram of the relevant section of the patient.

When more than one image reconstruction apparatus is used, as diagrammatically shown in FIG. 1 and 2, a plurality of images of different sections of an object can be produced simultaneously.

It is clear that, to produce a tomogram, the patient must be rotated about an axial axis, or the entire apparatus must be rotated around the patient. This is shown in the figure by an arrow.

FIG. 2 of the accompanying drawings shows a second embodiment of an apparatus according to the present invention. It is, the image intensifier tube 5 and the television pick-up tube 6 are coupled together not, as in the embodiment shown in FIG. 1, by fibre-optics means, but through a lens system 10. Where this variant is further similarly constructed to the first embodiment described above, a description of the constituent components will not be given. The operation of the second embodiment also corresponds to that of the first embodiment. Corresponding parts are, for that matter, designated by like reference numerals.

FIG. 3 of the accompanying drawings shows a variant of a part of the apparatus shown in FIGS. 1 and 2, in which the X-ray screen is coupled to the photocathode of image intensifier 5 not, as in the embodiment described before, by means of a lens system 4, but by means of a fibre-optics arrangement 11. Inasmuch as the construction of this embodiment is otherwise entirely similar to that of the two earlier described embodiments, FIG. 3 only shows the relevant part of the apparatus, using the same reference numerals as in FIGS. 1 and 2 for designating corresponding parts.

It will be clear from the above that, by virtue of the fact that a larger portion of the patient is scanned simultaneously than in the case of an array of discrete radiation detectors, a favourable load condition for the radiation source and/or the patient is achieved. Furthermore, in connection with the fact that all information for the image reconstruction apparatus is contained in a single video signal, only one logarithmic amplifier 7 is needed for converting the X-ray attenuation signal into an X-ray absorption signal.

Moreover, the video signals can be pre-processed, so that subsequent processing can be effected more rapidly and in a simpler manner.

Figure 4:
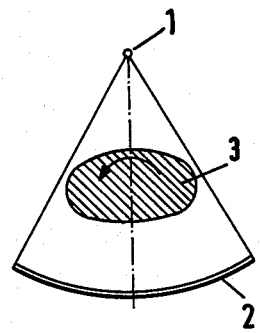
FIG. 4 shows a modification of a part of the apparatus shown in FIGS. 1, 2 and 3.

Although, in FIGS. 1, 2 and 3, the X-ray screen 2 is shown to be flat, the screen may be concavely curved towards the patient 3 and the source 1, as shown in FIG. 4. Such a construction leads to more uniform resolution, and freedom of geometrical distortion which is an advantage over an intensifier tube with a flat screen and a direct X-ray image intensifier tube.

Another advantage of an external screen over a direct X-ray image intensifier tube is that the screen may be exchangeable, which offers the possibility of using a special screen in certain cases, for example, a compartmented X-ray screen, possibly in combination with a scatter screen.

Another possibility is to arrange two X-ray screens one behind the other for absorption of the soft radiation substantially in one screen and of the hard radiation substantially in the other, whereby more accurate image reconstruction can be achieved. The light from the two screens can then be separated by means of polarizers or using the fact that the screens emit at different wavelengths.

The foregoing shows that the apparatus according to this invention enables a relatively simple and inexpensive production of signals from which tomograms can be formed, and has a number of advantages over prior proposals which make for optimum operation.

We claim:

1. An apparatus for tomography, comprising
   an X-ray or gamma-ray source,
   one detector body, and
   an image reconstruction apparatus,
   wherein said detector body is a two-dimensional, continuous X-ray screen having dimensions selected in relation to the disposition of the object section to be examined and of the source of radiation relative to the detector body so that the projection of the object section, as far as its greatest cross-sectional dimension is concerned, is at least completely depicted on the detector body, and the dimension of the X-ray screen at right angles to said projection is sufficient to accommodate at least two such projections of adjacent object sections.

2. An apparatus according to claim 1, wherein said detector is concave towards the source.

3. An apparatus according to claim 1, wherein said detector is exchangeable.

4. An apparatus for tomography, comprising
   an X-ray or gamma-ray source,
   one detector body,
   a luminance intensifier tube having an envelope,
   optical means for depicting the side of the detector body away from the source of radiation on the cathode of the luminance intensifier tube, and
   an image reconstruction apparatus,
   said detector body being arranged outside said envelope and being a two-dimensional, continuous X-ray screen having dimensions selected in relation to the disposition of the object section to be examined and of the source of radiation relative to the detector body so that the projection of the object section, as far as its greatest cross-sectional dimension is concerned, is at least completely depicted on the detector body, and the dimension of the X-ray screen at right angles to said projection is sufficient to accommodate at least two such projections of adjacent object sections.

5. An apparatus according to claim 4 wherein the detector body includes two X-ray screens one behind the other for absorption of soft radiation in the one screen and for absorption of hard radiation in the other screen; and means for separating light from the two screens.

6. An apparatus according to claim 4, further comprising a television pick-up tube having an input coupled by optical means to the anode end of the luminance intensifier tube, and an output coupled to the image reconstruction apparatus.

7. An apparatus according to claim 6, wherein said optical means are fibre-optical means.

8. An apparatus according to claim 6, wherein said optical means are lens means.

9. An apparatus according to claim 6, further comprising a television monitor coupled to an output terminal of said television pick-up tube.

10. An apparatus according to claim 6, wherein the image reconstruction apparatus includes a plurality of image reconstruction apparatuses coupled to the output of the television pick-up tube for simultaneously producing images of different sections of the object to be examined.

11. An apparatus according to claim 10, further comprising a logarithmic amplifier interconnected between the output of the television pick-up tube and the plurality of image reconstruction apparatuses for simultaneously producing images of different sections of the object to be examined.

12. An apparatus for tomography, comprising
    an X-ray or gamma-ray source,
    one detector body,
    a luminance intensifier tube having an input window,
    said input window being a fibre-optics arrangement for transmitting the radiation image from said detector body to the cathode surface of said luminance intensifier tube, and
    an image reconstruction apparatus,
    said detector body being arranged on the exterior surface of said input window and being a two-dimensional, continuous X-ray screen having dimensions selected in relation to the disposition of the object section to be examined and of the source of radiation relative to the detector body so that the projection of the object section, as far as its greatest cross-sectional dimension is concerned, is at least completely depicted on the detector body, and that the dimension of the X-ray screen at right angles to said projection is sufficient to accommodate at least two such projections of adjacent object sections.

13. An apparatus according to claim 12 wherein the detector body includes two X-ray screens one behind the other for absorption of soft radiation in the one screen and for absorption of hard radiation in the other screen, and means for separating light from the two screens.

14. An apparatus according to claim 12, further comprising a television pick-up tube having an input coupled by optical means to the anode end of the luminance intensifier tube, and an output coupled to the image reconstruction apparatus.

15. An apparatus according to claim 14, wherein said optical means are fibre-optical means.

16. An apparatus according to claim 14, wherein said optical means are lens means.

17. An apparatus according to claim 14, further comprising a television monitor coupled to an output terminal of said television pick-up tube.

18. An apparatus according to claim 14, wherein the image reconstruction apparatus includes a plurality of image reconstruction apparatuses coupled to the output of the television pick-up tube for simultaneously producing images of different sections of the object to be examined.

19. An apparatus according to claim 18, further comprising a logarithmic amplifier interconnected between the output of the television pick-up tube and the plurality of image reconstruction apparatuses for simultaneously producing images of different sections of the object to be examined.

* * * * *